US009557333B2

(12) United States Patent
Vivier et al.

(10) Patent No.: US 9,557,333 B2
(45) Date of Patent: Jan. 31, 2017

(54) METHODS OF TREATING GASTROINTESTINAL SARCOMA PATIENTS DEPENDING ON THEIR SB7H6 SERUM LEVEL

(71) Applicants: INSTITUT GUSTAVE ROUSSY, Villejuif (FR); INSERM (INSTITUT NATIONAL DE LA SANTE ET DE LA RECHERCHE MEDICALE), Paris (FR)

(72) Inventors: Eric Vivier, Cassis (FR); Laurence Zitvogel, Paris (FR)

(73) Assignees: INSTITUT GUSTAVE ROUSSY, Villejuif (FR); INSERM (INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 0 days.

(21) Appl. No.: 14/429,789

(22) PCT Filed: Sep. 20, 2013

(86) PCT No.: PCT/EP2013/069566
§ 371 (c)(1),
(2) Date: Mar. 20, 2015

(87) PCT Pub. No.: WO2014/044791
PCT Pub. Date: Mar. 27, 2014

(65) Prior Publication Data
US 2015/0233928 A1 Aug. 20, 2015

(30) Foreign Application Priority Data

Sep. 21, 2012 (EP) .................... 12306143

(51) Int. Cl.
*G01N 33/574* (2006.01)
(52) U.S. Cl.
CPC .. *G01N 33/57438* (2013.01); *G01N 33/57407* (2013.01); *G01N 33/57446* (2013.01); *G01N 2333/70532* (2013.01); *G01N 2333/70539* (2013.01); *G01N 2500/10* (2013.01); *G01N 2800/52* (2013.01)

(58) Field of Classification Search
None
See application file for complete search history.

(56) References Cited

U.S. PATENT DOCUMENTS

2008/0286825 A1  11/2008  Bottaro et al.

FOREIGN PATENT DOCUMENTS

WO  WO 2011/070443  6/2011

OTHER PUBLICATIONS

Brandt, C. S. et al. "The B7 family member B7-H6 is a tumor cell ligand for the activating natural killer cell receptor N-Kp30 in humans" *The Journal of Experimental Medicine*, Jul. 6, 2009, pp. 1495-1503, vol. 206, No. 7.
Delahaye, N. et al. "Alternatively spliced NKp30 isoforms affect the prognosis of gastrointestinal stromal tumors" *Nature Medicine*, Jun. 1, 2011, pp. 700-707, vol. 17, No. 6.
Written Opinion in International Application No. PCT/EP2013/069566, Mar. 31, 2014, pp. 1-10.

*Primary Examiner* — Elly-Gerald Stoica
(74) *Attorney, Agent, or Firm* — Saliwanchik, Lloyd & Eisenschenk

(57) ABSTRACT

The present invention relates to a method of predicting or monitoring the sensitivity of a subject having a tumor to a chemotherapy, a method of selecting an appropriate chemotherapeutic treatment of cancer, a method of screening or identifying a compound suitable for improving the treatment of a cancer, and corresponding kits. The method of predicting or monitoring the sensitivity of a subject having a tumor to a chemotherapy typically comprises a step a) of determining, in a biological sample from said subject, the presence, absence or expression level of at least one of a soluble B7H6 (sB7H6 or sB7-H6) and a soluble MIC (sMIC) and, when the expression level is determined, a step b) of comparing said expression level to a reference expression level, thereby assessing or monitoring whether the subject having a tumor is responsive or resistant to the chemotherapy.

5 Claims, 9 Drawing Sheets

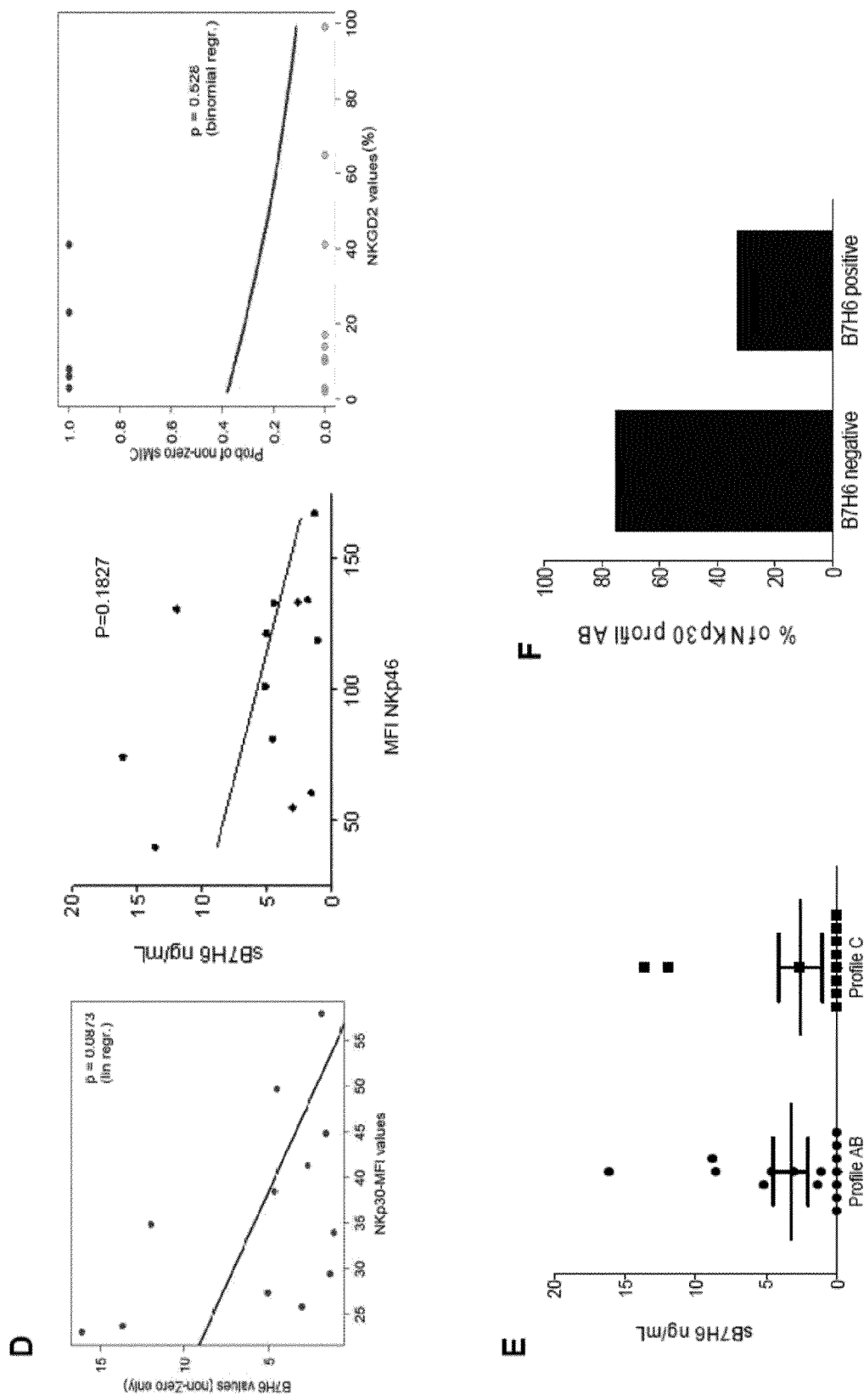
FIGURE 2 (Following)

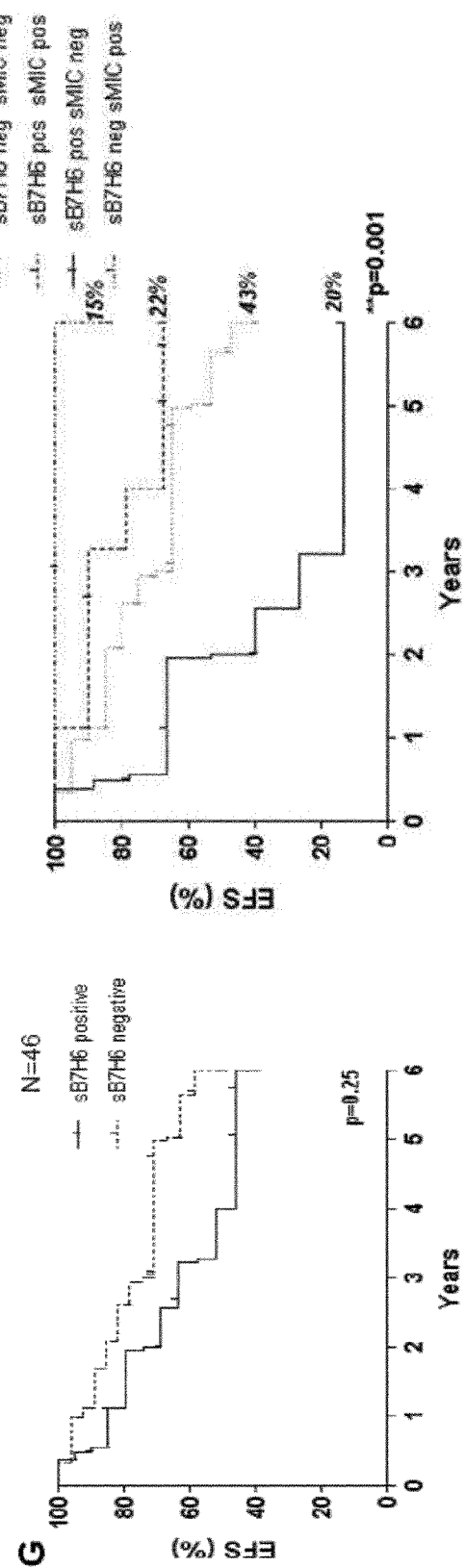
FIGURE 2 (Following)

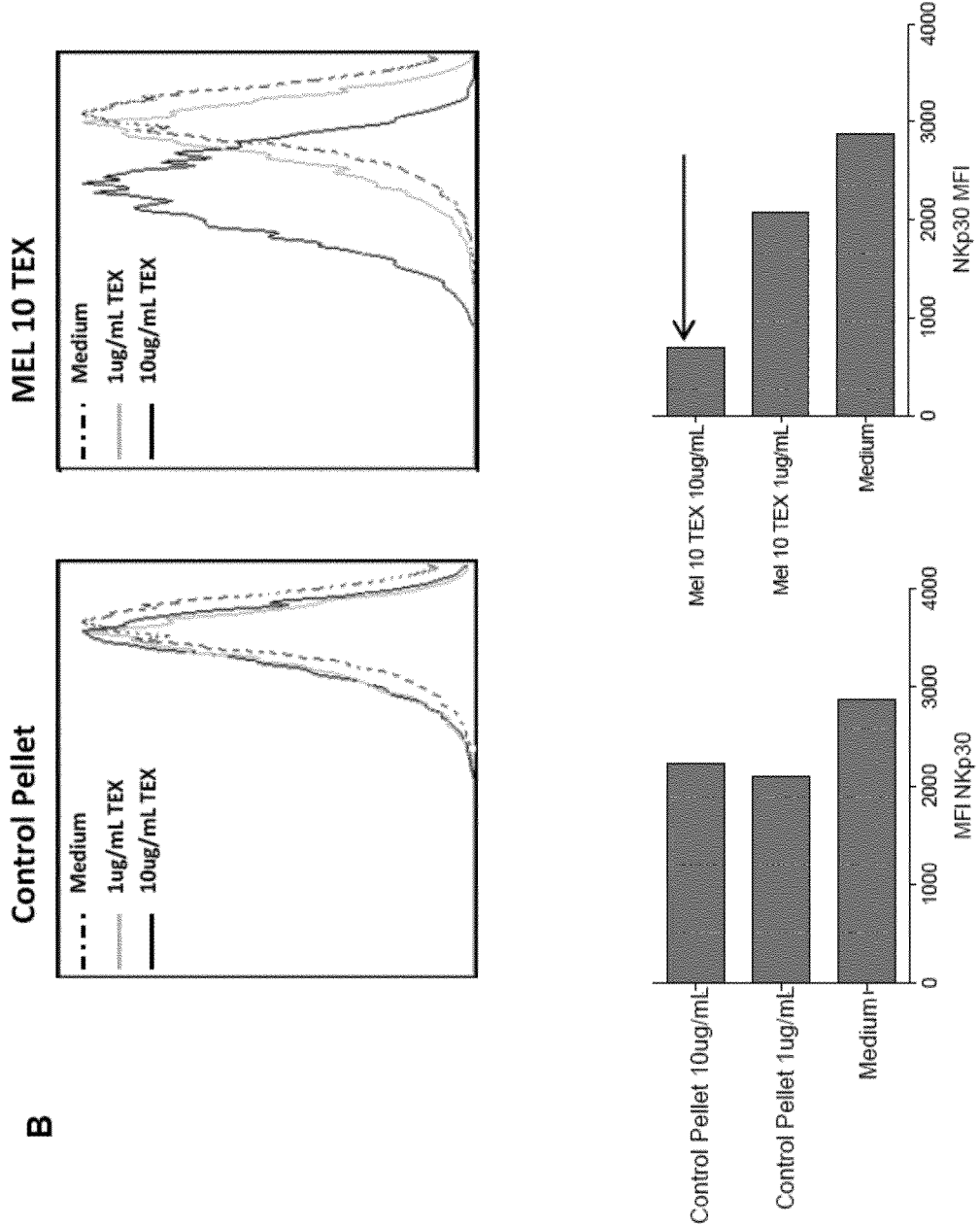
FIGURE 3 (Following)

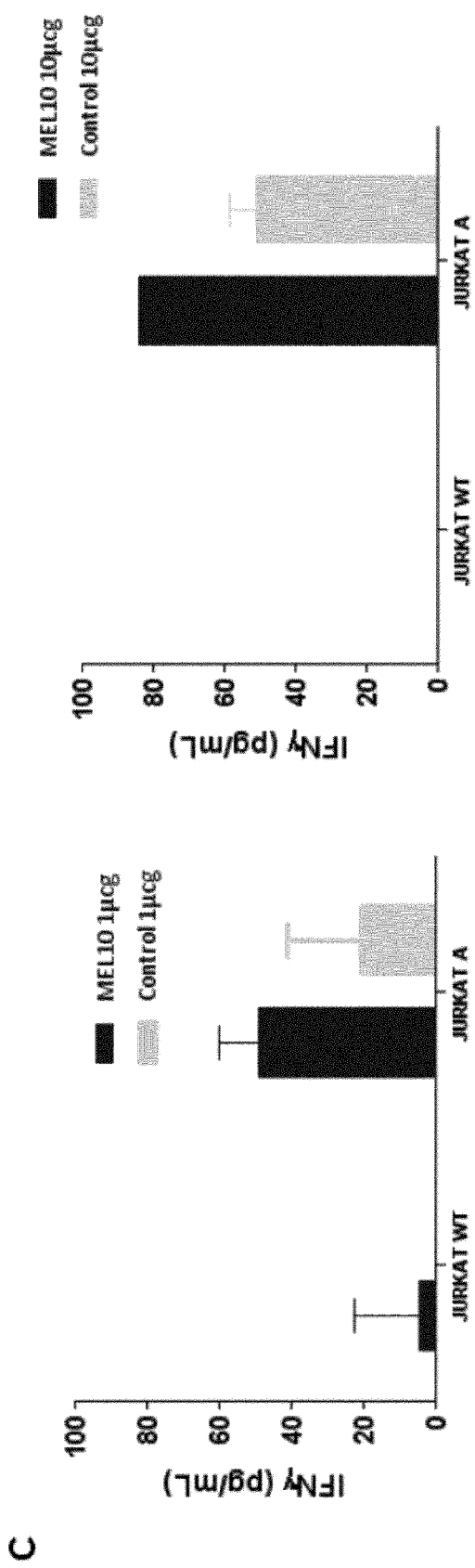
FIGURE 3 (Following)

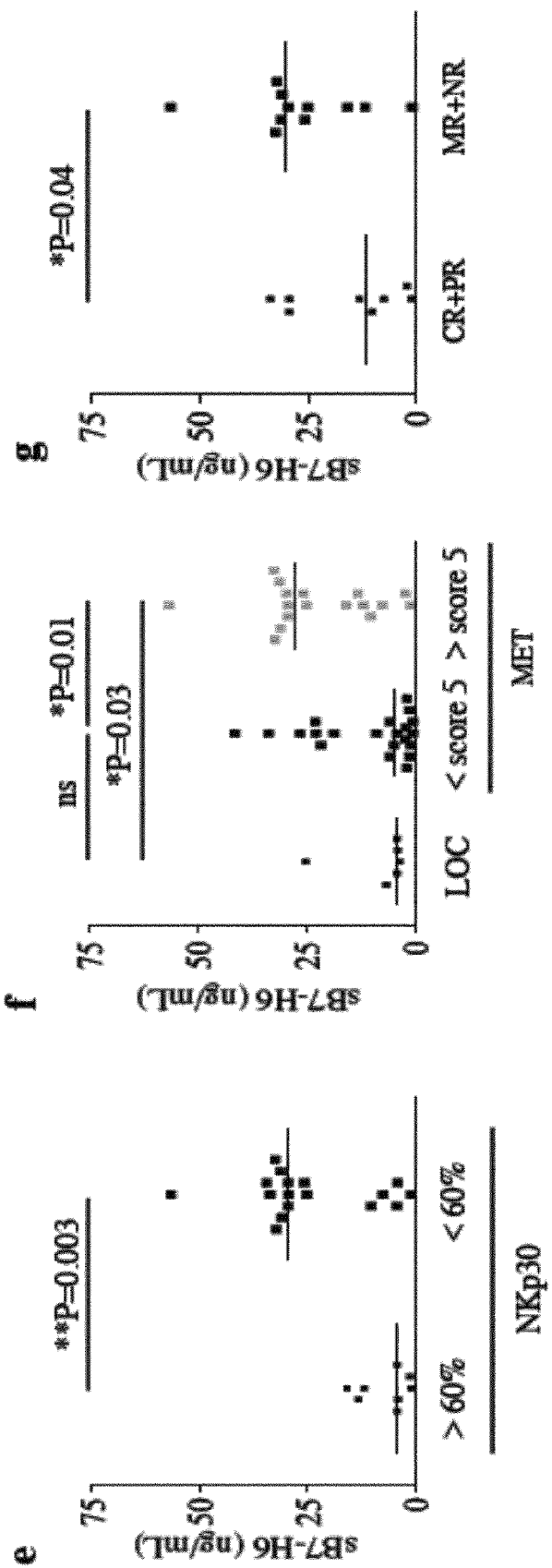
FIGURE 4 (Following)

ated for up to 24 hours. The culture supernatant of 293T-B7-H6 cells provides an additional source of sB7-H6.

METHODS OF TREATING GASTROINTESTINAL SARCOMA PATIENTS DEPENDING ON THEIR SB7H6 SERUM LEVEL

CROSS-REFERENCE TO RELATED APPLICATION

This application is the U.S. national stage application of International Patent Application No. PCT/EP2013/069566, filed Sep. 20, 2013.

FIELD OF THE INVENTION

The present invention relates to a method of predicting or monitoring the sensitivity of a subject having a tumor to chemotherapy, a method of selecting an appropriate chemotherapeutic treatment of cancer, a method of screening or identifying a compound suitable for improving the treatment of a cancer, and corresponding kits. The method of predicting or monitoring the sensitivity of a subject having a tumor to a chemotherapy typically comprises a step a) of determining, in a biological sample from said subject, the presence, absence or expression level of at least one of a soluble B7H6 (sB7H6 or sB7-H6) and a soluble MIC (sMIC) and, when the expression level is determined, a step b) of comparing said expression level to a reference expression level, thereby assessing or monitoring whether the subject having a tumor is responsive or resistant to the chemotherapy.

BACKGROUND OF THE INVENTION

B7-H6 is a member of the B7 family, which includes ligands (B7-1 and B7-2) for the T cell costimulatory receptor CD28 and the coinhibitory receptor CTLA-4, as well as ligands (PD-L1 and PD-L2) for the T cell coinhibitory receptor PD-1. Like all known B7 family members, B7-H6 comprises two Ig domains with adjacent phase 1 introns in the extracellular region. Importantly, B7-H6 was not detected in normal human tissues but was selectively expressed on a variety of human tumor cell lines, including T and B lymphomas, melanomas, and carcinomas (Brandt C S et al., 2009, J. Exp. Med., 206:1495). Furthermore, B7-H6 expression on tumor cells triggered NKp30-specific NK cell cytotoxicity and cytokine secretion. Thus, B7-H6 functions as a tumor-induced self-molecule that alerts innate immunity to cellular transformation via its interaction with the activating receptor NKp30 (Brandt C S et al., 2009, J. Exp. Med., 206:1495). B7-H6 transcripts have not been detected in most normal adult tissues, consistent with the absence of the protein on circulating cells isolated from healthy individuals.

As used herein, the term "MICA" refers to the MHC class I chain-related protein A encoded by the MICA gene (Gene ID: 100507436). As used herein, the term "MICB" refers to the MHC class I chain-related protein B encoded by the MICB gene (Gene ID: 4277). MICA and MICB are NKG2D ligands as defined above. MICA and MICB are highly related, sharing 85% amino acid identity. The term "MIC" refers to MICA and/or MICB.

"MIC" is a heavily glycosylated protein which is a ligand for the NKG2D type II receptor. Binding of the ligand activates the cytolytic response of natural killer (NK) cells, CD8 alpha beta T cells, and gamma delta T cells which express the receptor. This protein is stress-induced and is similar to MHC class I molecules.

Gastrointestinal stromal tumors (GISTs) are the most common mesenchymal tumors of the gastrointestinal tract. GISTs are thought to originate from the neoplastic transformation of the interstitial cells of Cajal, the intestinal pacemaker cells. The true incidence of GISTs remains unknown, but experience from clinical trials suggests an incidence of 4500-6000 new cases per year in the United States. The median age at diagnosis is approximately 58 years.

Historically, GISTs have been targeted by the three traditional cancer therapeutic modalities: surgery, chemotherapy, and radiotherapy. Surgery is effective for patients with resectable disease, but disease may recur in as many as 50% of individuals. Chemotherapy and radiotherapy have shown little efficacy (Joensuu H et al., 2002, Lancet Oncol, 3: 655). A major breakthrough occurred in 1998 with the discovery of gain-of-function mutations in the KIT oncogene in GISTs (Hirota S et al., 1998, Science, 279: 577). KIT encodes the transmembrane KIT receptor tyrosine kinase (CD117) that, when activated via binding by its ligand, regulates the intracellular signal transduction process. Constitutive tyrosine kinase activation by mutation results in unregulated cell growth and malignant transformation. More than 90% of GISTs harbour activating KIT mutations (Rubin B P et al., 2001, Cancer Res, 61: 8118). These mutations commonly occur in exon 11 (juxtamembrane domain) in 57-71% of cases, exon 9 (extracellular domain) in 10-18% of cases, exon 13 (tyrosine kinase domain I) in 1-4% of cases, and exon 17 (tyrosine kinase domain II) in 1-4% of cases (Raut C P et al., 2007, Curr Opin Gastroenterol, 23: 149). Approximately 35% of GISTs lacking KIT mutations have activating mutations in a gene encoding a related receptor tyrosine kinase, the platelet-derived growth factor receptor a (PDGFRA) (Heinrich M C et al., 2003, Science, 299: 708). PDGFRA mutations have been identified in exon 12 (1-2% of GISTs), exon 18 (2-6%), and exon 14 (<1%) (Corless C L et al., 2005, J Clin Oncol, 23: 5357). Identification of KIT and PDGFRA mutations led to the development of specific targeted therapies with tyrosine kinase inhibitors (TKIs). Therapy with the TKIs imatinib mesylate (STI571, Gleevec-Novartis) and sunitinib malate (SU11248, Sutent-Pfizer) is effective for unresectable, metastatic, and recurrent disease (Heinrich M C et al., 2003, J Clin Oncol, 21: 4342). Imatinib selectively inhibits several tyrosine kinases including KIT, PDGFRA, and ABL. Data from a phase II imatinib trial revealed that mutational status of KIT was the most important factor predictive of clinical response to imatinib (Heinrich M C et al., 2003, J Clin Oncol, 21: 4342). Patients with GISTs expressing exon 11 KIT mutants who received imatinib had a substantially higher partial response rate, longer median survival, and less likelihood of progressing than those with GISTs expressing wild-type or exon 9 KIT mutants. Imatinib is a dramatically effective agent, but the duration of its benefits is finite. The second targeted tyrosine kinase inhibitor, sunitinib malate, has been approved for the treatment of imatinib-resistant GISTs after recent encouraging results (Rubin B P et al., 2007, Lancet, 369: 1731). However, as explained previously, drug resistance is an increasingly more common phenomenon (Van Glabbeke M et al., 2005, J Clin Oncol, 23: 5795).

Renal cell carcinoma (RCC, also known as hypernephroma) is a renal cancer that originates in the lining of the proximal convoluted tubule, the very small tubes in the kidney that filter the blood and remove waste products. RCC is the most common type of kidney cancer in adults, responsible for approximately 80% of cases (Mulders P F et al., 2008, Ned Tijdschr Geneeskd, 152: 376). It is also known to be the most lethal of all the genitourinary tumors.

Initial treatment is most commonly a radical or partial nephrectomy and remains the mainstay of curative treatment (Rini B I et al., 2008, Curr Opin Oncol, 20: 300). Where the tumor is confined to the renal parenchyma, the 5-year survival rate is 60-70%, but this is lowered considerably where metastases have spread. It is relatively resistant to radiation therapy and chemotherapy, although some cases respond to immunotherapy. Targeted cancer therapies such as sunitinib, temsirolimus, bevacizumab, interferon-alpha, and sorafenib have improved the outlook for RCC (progression-free survival), although they have not yet demonstrated improved survival.

Whatever the nature of the cancer, the accurate selection of the patients capable of responding to a particular chemotherapy is a solution for them to receive the most appropriate therapy as soon as possible and typically as soon as they are diagnosed.

SUMMARY OF THE INVENTION

The present invention is based on the observation that B7-H6, previously known to be expressed on the surface of tumor cells as cell membrane-anchored polypeptides, may exist in a soluble form and may be distributed into the circulation ("soluble B7-H6"). Using a panel of monoclonal antibodies (mAbs) generated against B7-H6, the inventors analyzed the pathways that lead to the expression of B7-H6. In vivo, B7-H6 was associated with exosomes and was detected in the sera of a fraction of cancer patients. These findings reveal that sB7-H6 is a predicting marker of response to a chemotherapeutic treatment of cancer. The inventors further discovered the value of assessing sMIC in addition to sB7H6 in specific cancers. Thus, the present invention includes methods and kits for predicting or assessing the response of a subject having a tumor or cancer to a particular chemotherapeutic treatment using these biomarkers.

A first method herein described is an in vitro or ex vivo method of predicting (or assessing) or monitoring the sensitivity of a subject having a tumor to a chemotherapy, which method comprises a step a) of determining, in a biological sample from said subject, the presence, absence or expression level of at least one of a soluble B7H6 (sB7H6) and a soluble MIC (sMIC) and, when the expression level is determined, a step b) of comparing said expression level to a reference expression level, thereby assessing or monitoring whether the subject having a tumor is responsive or resistant to the chemotherapy.

A particular method herein described is an in vitro or ex vivo method of selecting an appropriate chemotherapeutic treatment of a renal cancer for a subject having a renal cancer, which method comprises a step a) of determining, in a biological sample of said subject, the expression level of soluble B7H6 (sB7H6) and a step b) of comparing said level to an sB7H6 reference expression level, i) an sB7H6 expression level above the sB7H6 reference expression level being the indication that a cytokine (for example IFNa and/or IL-2), an antiangiogenic drug (such as sorafenib), an mTOR inhibitor, a tyrosine kinase inhibitor (such as imatinib), or any combination thereof, will not be efficient in the subject; and a step c) of selecting a distinct chemotherapeutic treatment of the renal cancer, ii) an sB7H6 expression level below the sB7H6 reference expression level being the indication that a cytokine, an antiangiogenic drug, an mTOR inhibitor, a tyrosine kinase inhibitor, or any combination thereof will be efficient in the subject, said cytokine, antiangiogenic drug, mTOR inhibitor, tyrosine kinase inhibitor, or combination thereof being an appropriate chemotherapeutic treatment of the renal cancer.

Another particular method herein described is a method of selecting an appropriate chemotherapeutic treatment of a gastrointestinal sarcoma (GIST) for a subject having a GIST, which method comprises a step a) of determining, in a biological sample of said subject, the expression level of soluble B7H6 (sB7H6) and preferably in addition the presence or absence of soluble MIC (sMIC), and a step b) of comparing said level to an sB7H6 reference expression level, an sB7H6 expression level above the sB7H6 reference expression level being the indication that a tyrosine kinase inhibitor, in particular imatinib, will not be efficient alone in the subject, and an sB7H6 expression level above the sB7H6 reference expression level together with the absence of sMIC being the indication that a tyrosine kinase inhibitor, in particular imatinib, will not be efficient alone in the subject, and a step c) of selecting a distinct chemotherapeutic treatment of the GIST; on the contrary, an sB7H6 expression level below the sB7H6 reference expression level being the indication that a tyrosine kinase inhibitor, in particular imatinib, will be efficient in the subject, and an sB7H6 expression level below the sB7H6 reference expression level together with the presence of sMIC being the indication that a tyrosine kinase inhibitor, in particular imatinib, will be efficient (and in particular, as demonstrated by experiments, extremely efficient) in the subject, a tyrosine kinase inhibitor, in particular imatinib, being an appropriate chemotherapeutic treatment of the GIST cancer.

Also herein described is a method for screening or identifying a compound suitable for improving the treatment of a cancer in subject having a tumor, said method comprising determining the ability of a test compound to modify the expression of sB7H6 and/or of sMIC, or compensate for an abnormal expression thereof.

A further embodiment relates to a kit for assessing or monitoring the sensitivity of a subject having a tumor to a chemotherapy, wherein the kit comprises detection means selected from the group consisting of at least one antibody specific to sB7H6 and preferably in addition an antibody specific to sMIC, and, optionally, a leaflet providing the sB7H6 reference expression level in a control population.

DETAILED DESCRIPTION OF THE INVENTION

As used herein, the term "B7-H6" or "B7H6" was first described in Brandt C S et al. (2009, J. Exp. Med., 206:1495) and in U.S. Patent Application Publication No. 2009/0220502. An exemplary amino acid sequence is described in the UniProtKB/Swiss-Prot database under the accession number Q68D85.

A used herein, the term soluble "MIC" (sMIC) was first described in Groh V et al., 2002. Nature, 419: 734. Antibodies directed against sMIC have been described and generated by Dr. Sophie Caillat-Zücman (Hue S et al, 2004, Immunity; 21: 367). An exemplary amino acid sequence is described in the UniProtKB/Swiss-Prot database under the accession number Q29983 (MICA) and Q29980 (MICB).

In the present invention, the cancer is a cancer that is usually or conventionally treated with one of the following therapies: chemotherapy, radiotherapy, immunotherapy, specific kinase inhibitor-based therapy, antiangiogenic agent based-therapy, antibody-based therapy and surgery.

The cancer or tumor may be any kind of cancer or neoplasia. The tumor is typically selected from a carcinoma, a sarcoma, a lymphoma, a melanoma, a pediatric tumor and a leukemia tumor. The cancer is preferably selected from a gastrointestinal sarcoma (GIST), a renal cancer, a breast cancer, a leukemia, in particular an acute lymphoid leukemia, a Hodgkin's lymphoma, a neuroblastoma (NB), in particular a High Risk Neuroblastoma (HR-NB), a prostate cancer, an esophageal cancer, a colon cancer, a rectal cancer, a lung cancer, in particular a non-small cell lung cancer (NSCLC), a thyroid cancer, an osteosarcoma, and a melanoma.

In a preferred embodiment the cancer is of mesenchymal origin, and is typically selected from GIST and NB (in particular HR-NB).

In the context of conventional radiotherapy, the treatment may consist of exposing the subject to irradiation selected for example from XR, gamma irradiation and/or UVC irradiation.

Cancers sensitive to immunotherapy are conventionally treated using a compound selected for example from IL-2 (interleukin 2), IFN (interferon) alpha (IFNa), and a vaccine.

Cancers sensitive to a specific kinase inhibitor-based therapy are conventionally treated using a compound selected for example from a tyrosine kinase inhibitor, a serine kinase inhibitor and a threonine kinase inhibitor.

Cancers sensitive to an antibody-based therapy, preferably to a monoclonal antibody-based therapy, are conventionally treated using a specific antibody such as anti-CD20 (pan B-Cell antigen) or anti-Her2/Neu (Human Epidermal Growth Factor Receptor-2/NEU).

Preferably, the conventional treatment of cancer is a conventional chemotherapy. In the context of a conventional chemotherapy, the treatment may use a chemotherapeutic drug or agent, a cytotoxic agent or a cell death inducer, in particular a genotoxic agent. In a particular embodiment of the present invention, the chemotherapeutic agent is an agent selected for example from an anthracycline (DX, daunorubicin, idarubicin and MTX), an antimitotic agent (a spindle poison such as vincristine or vinblastine), a DNA intercalating agent, a taxane (such as docetaxel, larotaxel, cabazitaxel, paclitaxel (PG-paclitaxel and DHA-paclitaxel), ortataxel, tesetaxel, and taxoprexin), gemcitabine, etoposide, Mitomycin C, an alkylating agent, a platin-based component such as CDDP and OXP, and a TLR (Toll-like receptor)-3 ligand.

In a particular embodiment of the present invention, when the chemotherapeutic drug or agent (also herein generally identified as "chemotherapy") is administered to the subject before any surgical step, the chemotherapeutic agent is preferably selected from Imatinib (IM or Gleevec®), sunitinib, an anthracycline, a cytokine, an anti-angiogenic drug (sorafenib), a monoclonal antibody targeting an oncogene or an abnormal protein, and any combination thereof.

A particular renal cancer is a renal cancer conventionally treated with cytokines or anti-angiogenic drugs (sorafenib), such as metastatic renal cancer.

A particular gastrointestinal stromal tumor (GIST) is a GIST conventionally treated with a tyrosine kinase inhibitor (such as imatinib (Gleevec®), sunitinib, nilotinib, dasatinib, sorafenib, regorafenib, vatalanib, masitinib, pazopanib, or crenolanib), a HSP90 inhibitor (such as STA-9090, AT-13387, or AUY922), a monoclonal antibody (such as anti-VEGF bevacizumab or anti-PGDFRA IMC-3G3 (Olaratumab)), an mTOR inhibitor (such as everolimus), an anthracycline, or another molecule selected for example from perifosine, anti-AKT or a drug reprogramming macrophages, anti-CSF-1 antibody, anti-CXCR4 antibody, or anti-CXCL1/CXCR2 antibody.

In the context of the present invention, the patient or subject is a mammal. In a particular embodiment, the mammal is a human being of any age or sex. The patient typically has a tumor. Unless otherwise specified in the present disclosure, the tumor is a cancerous or malignant tumor. Preferably the subject is a subject who has not been previously exposed to a treatment of cancer or a subject who has received the first administration of a chemotherapeutic drug.

In the context of renal cancer, a particular subpopulation of subjects is composed of high or intermediate risk of relapse subjects according to the Motzer classification (Motzer R J et, al., 1999, J Clin Oncol, 17:2530). These subjects are distinct from the subjects classified as low risk of relapse subjects according to said classification.

In the context of GIST, a particular subpopulation of subjects is composed of metastatic GIST as well as high or intermediate risk of relapse (score 3) GIST subjects, typically localized (non-metastatic) GIST subjects, according to the Miettinen score (Miettinen M et al, 2003, Am J Surg Pathol, 27: 625; Miettinen M et al, 2006, Am J Surg Pathol, 30: 477; Miettinen M et al, 2005, Am J Surg Pathol, 29: 52). Another particular subpopulation of subjects is composed of subjects having metastases.

Implementations of the methods of the invention involve obtaining a (biological) sample from a subject. The sample is preferably a fluid sample and may include serum, blood, plasma, lymphatic fluid, spinal fluid, pleural effusion, ascites, or a combination thereof. Cells are not included in the sample because these embodiments involve assaying for soluble, as opposed to cell-bound, B7-H6 or MIC. A preferred sample is thus a fluid sample without cells.

A method according to the present invention is an in vitro or ex vivo method of predicting (or assessing) or monitoring the sensitivity of a subject having a tumor (such as herein described) to a chemotherapy, which method comprises a step a) of determining, in a biological sample from said subject, the presence, absence or expression level of at least one of a soluble B7H6 (sB7H6) and a soluble MIC (sMIC) and, when the expression level is determined, a step b) of comparing said expression level to a reference expression level, thereby assessing or monitoring whether the subject having a tumor is responsive or resistant to the chemotherapy.

By "sensitivity" or "responsiveness" is intended herein the likelihood that a patient will respond to a chemotherapeutic treatment.

By "resistant" is intended herein the likelihood that a patient will not respond to a chemotherapeutic treatment.

Predictive methods of the invention can be used clinically to make treatment decisions by choosing as soon as possible the most appropriate treatment modalities for a particular patient.

If the subject is identified, using a method according to the present invention, as resistant to a particular treatment of cancer, the method advantageously further comprises a step of selecting a distinct chemotherapeutic treatment, typically involving a "compensatory molecule", such as a neutralizing anti-sB7-H6 antibody (see below), to be used in combination with the originally preselected chemotherapeutic drug or with a distinct chemotherapeutic drug as the appropriate therapeutic treatment of cancer for the subject.

Preferably, the step of determining the presence, absence or expression level of at least one of sB7H6 and sMIC in a biological sample of the subject is performed before any chemotherapeutic treatment step. Less preferably but also possibly, this step can be performed after the first administration of a chemotherapeutic drug to the subject. This step is also preferably performed before any surgical tumor resection.

In a particular embodiment, the method according to the present invention is an in vitro or ex vivo method of predicting or monitoring the sensitivity of a subject having a sarcoma, preferably a gastrointestinal sarcoma (GIST), and the chemotherapy is selected from imatinib (Gleevec®), sunitinib, an anthracycline and any combination thereof.

In another embodiment, the method according to the present invention is an in vitro or ex vivo method of predicting or monitoring the sensitivity of a subject having a renal cancer, preferably a metastatic renal cancer, and the chemotherapy is preferably selected from a cytokine, an anti-angiogenic drug (such as sorafenib), an mTOR inhibitor and any combination thereof.

Herein described is a method wherein the cancer is renal cancer (RCC), in particular a metastatic renal cancer, and the method comprises a step a) of determining, in a biological sample of the subject, the expression level of sB7H6 and a step b) of comparing said level to a reference expression level or reference value, an expression level (as measured in the biological sample) above the reference expression level being indicative of resistance of the subject to the chemotherapy.

Typically, the "reference value" or "reference expression level" is the level of the soluble B7-H6 polypeptide in a control sample derived from one or more subjects (reference population) having a cancer, and is typically the median value when obtained from the reference population.

As an example, when the patient is bearing a metastatic RCC cancer, and the candidate chemotherapeutic drug (herein identified as chemotherapy) being selected from an anti-angiogenic drug and an mTOR inhibitor such as herein described, the reference expression level is between 3 and 5 ng/ml, and is preferably of about 4 ng/ml.

Further herein described is a method wherein the cancer is a gastrointestinal stromal tumor (GIST), in particular a metastatic GIST, and the method comprises a step a) of determining, in a biological sample of the subject, the expression level of sB7H6 and a step b) of comparing said level to a sB7H6 reference expression level, an expression level above the reference expression level being indicative of resistance of the subject to the chemotherapy.

As an example, when the patient is bearing a metastatic GIST, and the candidate chemotherapeutic drug (herein identified as chemotherapy) being imatinib, the reference expression level is between 0 and 4 ng/ml, preferably between 0 and 3 ng/ml, and even more preferably of about 3 ng/ml.

In a preferred embodiment, the previously described method further comprises a step of determining, in a biological sample of the subject, the presence or absence of sMIC, the absence of sMIC together with an sB7H6 expression level above the sB7H6 reference expression level being indicative of resistance of the subject to the chemotherapy. On the contrary, the presence of sMIC together with an sB7H6 expression level below the sB7H6 reference expression level being indicative that the chemotherapy will be efficient in said subject.

In some embodiments of the invention, identification of a soluble B7-H6 polypeptide or soluble MIC polypeptide involves the use of at least one B7-H6 or MIC polypeptide binding agent. Furthermore, it is contemplated that a B7-H6 or MIC polypeptide binding agent may or may not be specific to sB7-H6 or sMIC. For example, the B7-H6 (or MIC) polypeptide binding agent may bind to a part of B7-H6 (or MIC) (e.g., an epitope) that is not available when B7-H6 (or MIC) is bound to a cell. Alternatively, different conformations may serve as the basis for binding agents capable of distinguishing between soluble and bound B7-H6 or MIC.

The polypeptide is, in particular embodiments, an antibody. In further embodiments in relation with B7-H6, the antibody is a monoclonal antibody, such as those described in the International Patent Publication WO2011070443. In particular the antibody may be 17B1.3 mAb (Deposit No. CNCM 1-4245). The antibody can be bi-specific, recognizing two different epitopes. The antibody, in some embodiments, immunologically binds to more than one epitope from the same soluble B7-H6 polypeptide.

In other embodiments in relation with MIC, the antibody is for example SR99 mAb (Hue S et al, 2003, J. Immunol, 171:1909).

A B7-H6 polypeptide binding agent that is a polypeptide may also include all or part of NKp30, which is a receptor for B7-H6 polypeptides.

A MIC polypeptide binding agent that is a polypeptide may also include all or part of NKG2D, which is a receptor for MIC polypeptides.

In some embodiments of the invention, the soluble B7-H6 or MIC polypeptide binding agent is an aptamer.

In some embodiments of the invention, the soluble B7-H6 or MIC binding agent is labeled. In further embodiments, the label is radioactive, fluorescent, chemiluminescent, an enzyme, or a ligand. It is also specifically contemplated that a binding agent is unlabeled, but may be used in conjunction with a detection agent that is labeled. A detection agent is a compound that allows for the detection or isolation of itself so as to allow detection of another compound that it binds, directly or indirectly. An indirect binding refers to binding among compounds that do not bind each other directly but associate or are in a complex with each other because they bind the same compounds or compounds that bind each other.

Other embodiments of the invention involve a second B7-H6 (or MIC) polypeptide binding agent in addition to a first B7-H6 (or MIC) polypeptide binding agent. The second binding agent may be any of the entities discussed above with respect to the first binding agent, such as an antibody. It is contemplated that a second antibody may bind to the same or different epitopes as the first antibody. It is also contemplated that the second antibody may bind the first antibody or another epitope than the one recognized by the first antibody.

As discussed earlier, binding agents may be labeled or unlabeled. Any B7-H6 (or MIC) polypeptide binding agent used in methods of the invention may be recognized using at least one detection agent. A detection agent may be an antibody that binds to a B7-H6 (or MIC) polypeptide binding agent, such as an antibody. The detection agent antibody, in some embodiments, binds to the Fc region of a binding agent antibody. In further embodiments, the detection agent is biotinylated, which is incubated, in additional embodiments, with a second detection agent comprising streptavidin and a label. It is contemplated that the label may be radioactive, fluorescent, chemiluminescent, an enzyme, or a ligand. In some cases, the label is an enzyme, such as horseradish peroxidase.

The present invention also covers methods involving using an ELISA to identify a soluble B7-H6 or a soluble MIC polypeptide. In some embodiments, the ELISA is a sandwich assay. In a sandwich assay, more than one antibody will be employed. Typical ELISA methods can be used, wherein the wells of a microtiter plate are coated with a set of antibodies which recognize the protein of interest. A sample containing or suspected of containing the protein of interest is then added to the coated wells. After a period of incubation sufficient to allow the formation of antibody-antigen complexes, the plate(s) can be washed to remove unbound moieties and a detectably labeled secondary binding molecule added. The secondary binding molecule is allowed to react with any captured sample marker protein, the plate is washed and the presence of the secondary binding molecule is detected using methods well-known in the art.

Other methods of the invention further include assaying a sample for a cell-bound B7-H6 (or MIC) polypeptide in addition to a soluble polypeptide. The second assay may be performed on the same sample as the identification of a soluble B7-H6 (or MIC) polypeptide or it may be performed on a different sample. It is contemplated that a sample may or may not include cells.

Also herein described is a method of selecting an appropriate chemotherapeutic treatment of a renal cancer for a subject having a renal cancer, in particular a metastatic renal cancer, which method comprises a step a) of determining, in a biological sample of said subject, the expression level of soluble B7H6 (sB7H6) and a step b) of comparing said level to an sB7H6 reference expression level, i) an sB7H6 expression level above the sB7H6 reference expression level being the indication that a cytokine (such as IFNa and/or IL-2), an anti-angiogenic drug (such as sorafenib), an mTOR inhibitor, a tyrosine kinase inhibitor, or any combination thereof will not be efficient in the subject, and a step c) of selecting a distinct chemotherapeutic treatment of the renal cancer, ii) a sB7H6 expression level below the sB7H6 reference expression level being the indication that a cytokine, an anti-angiogenic drug, an mTOR inhibitor, a tyrosine kinase inhibitor, or any combination thereof will be efficient in the subject, said cytokine, anti-angiogenic drug, mTOR inhibitor, tyrosine kinase inhibitor, or any combination thereof being an appropriate chemotherapeutic treatment of the renal cancer.

In a particular embodiment in relation with the previously described method, when the cytokine, the anti-angiogenic drug, the mTOR inhibitor or a combination thereof is not efficient alone in the subject, the distinct chemotherapeutic treatment is a combination of the cytokine, the anti-angiogenic drug, the mTOR inhibitor or the combination thereof with an anti-B7-H6 neutralizing antibody together with any one of an anti-PDL1 antibody, an anti-PDL2 antibody and a cancer vaccine, said cancer vaccine being associated with cyclophosphamide.

Another particular method herein described is a method of selecting an appropriate chemotherapeutic treatment of a gastrointestinal stromal tumor (GIST), in particular a metastatic GIST, for a subject having a GIST, in particular a metastatic GIST, which method comprises a step a) of determining, in a biological sample of said subject, the expression level of soluble B7H6 (sB7H6) and preferably in addition the presence or absence of soluble MIC (sMIC), and a step b) of comparing said level to an sB7H6 reference expression level, an sB7H6 expression level above the sB7H6 reference expression level being the indication that a tyrosine kinase inhibitor, in particular imatinib, will not be efficient alone in the subject, and an sB7H6 expression level above the sB7H6 reference expression level together with the absence of sMIC being the indication that a tyrosine kinase inhibitor, in particular imatinib, will not be efficient alone in the subject, and a step c) of selecting a distinct chemotherapeutic treatment of the GIST; on the contrary, an sB7H6 expression level below the sB7H6 reference expression level being the indication that a tyrosine kinase inhibitor, in particular imatinib, will be efficient in the subject, and an sB7H6 expression level below the sB7H6 reference expression level together with the presence of sMIC being the indication that a tyrosine kinase inhibitor, in particular imatinib, will be efficient (and in particular, as demonstrated by experiments, extremely efficient) in the subject, a tyrosine kinase inhibitor, in particular imatinib, being an appropriate chemotherapeutic treatment of the GIST, in particular of the metastatic GIST.

In the methods herein described of assessing the sensitivity of a subject having a tumor to a chemotherapy as well as in the methods herein described of selecting an appropriate chemotherapeutic treatment, any classical method known by the skilled person of determining the presence or measuring the expression level of a compound of interest, such as, typically, ELISA and radioimmunoassay, can be used.

In some embodiments the invention relates to a method for monitoring the treatment of a subject suffering from an inflammatory condition comprising i) determining the level of a soluble B7-H6 polypeptide in a sample obtained from the subject before the treatment, ii) determining the level of a soluble B7-H6 polypeptide in a sample obtained from the subject before the treatment, iii) comparing the level determined at step i) with the level determined at step ii) and iv) concluding that treatment is effective when the level determined at step ii) is lower than the level determined at step i) or concluding that the treatment is not effective when the level determined at step ii) is the same as the level determined at step i) or is higher than the level determined at step i).

A method of selecting an appropriate, preferably optimal, therapeutic treatment of cancer for a subject having a tumor, as herein described, is in addition herein described, as well as appropriate chemotherapeutic treatment involving for example compensatory molecules for use in such a treatment of cancer, preferably in combination with the preselected chemotherapeutic drug, in a subject identified, using a method as herein described, as resistant to said preselected chemotherapeutic drug.

When the tyrosine kinase inhibitor, typically imatinib, is not efficient alone in the subject, typically in a subject suffering from a GIST, the distinct chemotherapeutic treatment is a combination of the tyrosine kinase inhibitor and a compound selected from: anti-B7-H6 neutralizing antibody (Ab) and a immunomodulator stimulating T and/or NK cell production or activity, such as an anti-PD-1 Ab (Programmed cell death protein 1), an anti-PDL-1 Ab (Programmed cell death protein ligand 1), an anti-PDL2 Ab (Programmed cell death protein ligand 2), an anti-CTLA4 (Cytotoxic T-Lymphocyte Antigen 4) monoclonal Ab (Ipilimumab/YERVOY), a double-strand RNA (Poly I:C Oncovir®, Poly A:U), a type 1 IFN (interferon) (alpha2b), IL-2 (interleukin 2), an inhibitor of IL-1/IL-1R1, an inhibitor of TNFa/TNFR, a TLR7 antagonist, a TLR8 antagonist, a TLR9 antagonist, and any combination thereof. The previous list of compounds which can be combined with the tyrosine kinase inhibitor can further include for example an anti-TRAIL (TNF-related apoptosis-inducing ligand) Ab, an anti-FasL (Fas ligand) Ab, an anti-IL-10 Ab, an anti-IL-23 Ab, and any combination thereof.

As for RCC, when conventional therapy (cytokine, anti-angiogenic drug, mTOR inhibitor, tyrosine kinase inhibitor (TKI), or a combination thereof) is not efficient alone, the distinct chemotherapeutic treatment is advantageously a combination of said conventional therapy with an anti-B7-H6 neutralizing antibody together with any one of an anti-PDL1 Ab, an anti-PDL2 Ab, and a cancer vaccine, said cancer vaccine being associated with cyclophosphamide.

For subject suffering from a GIST or RCC, any one of a TLR- (Toll-like receptor) 7, TLR-8, or TLR-9 antagonist, as well as a TNF (tumor necrosis factor)-alpha inhibitor or IL1R1/IL-1 inhibitor (Anakinra or equivalent), is a good candidate to suppress the accumulation of sB7-H6 molecules in the serum of GIST or RCC patients (see below). Anti-inflammatory compounds, preferentially non-steroidal anti-inflammatory compounds, but also NFkB (nuclear factor-kappa B) or STAT3 (signal transducers and activators of transcription) inhibitors or agents restoring autophagy (resveratrol, spermidine, rapamycin, curcumin, etc.) will decrease sB7-H6 levels and synergize with anti-sB7-H6 antibodies or conventional therapies as previously defined. Also, any compound that reduces the exosome secretion, such as amiloride (3,5-diamino-6-chloro-N-(diaminomethylidene) pyrazine-2-carboxamide; Modamide) (Chalmin F et al., 2010, J Clin Invest., 120:457), can be advantageously used with anti-sB7-H6 antibodies or conventional therapies as previously defined.

Methods of screening for candidate therapeutic agents for preventing or treating cancer are also included as part of the invention. The method is typically performed in vitro or ex vivo. When performed ex vivo, it can be performed for example on a sample from a subject who has been administered with a test compound.

A method herein described is a method for screening or identifying a compound suitable for improving the treatment of a cancer in a subject having a tumor, said method comprising determining the ability of a test compound to modify the expression of sB7H6 and/or of sMIC, or compensate for an abnormal expression thereof.

In some embodiments, the present invention relates to a method of screening for candidate therapeutic agents for a cancer, comprising i) providing a plurality of candidate compounds, ii) bringing the candidate compounds into contact with cancer cell lines expressing B7-H6 and producing sB7-H6 in the supernatants in presence of an agent that blocks the expression of a soluble B7-H6 polypeptide, iii) determining the level of the soluble B7-H6 polypeptide expressed by the cancer cells, iv) comparing the level determined at step iii) with the level determined in the absence of the candidate compounds, and v) and positively selecting the candidate compounds when the level determined at step iii) is lower than the level determined in the absence of the candidate compounds.

Typically, the agent that blocks the expression of a soluble B7-H6 polypeptide is selected from the group consisting of a TLR7 antagonist, TLR-8 antagonist, TLR-9 antagonist, TNF-alpha inhibitor or IL1R1/IL-1 inhibitor (Anakinra or equivalent).

Typically the candidate compound may be selected from the group consisting of peptides, peptidomimetics, small organic molecules, antibodies, aptamers or nucleic acids. For example, the candidate compound according to the invention may be selected from a library of compounds previously synthesized, or a library of compounds for which the structure is determined in a database, or from a library of compounds that have been synthesized de novo.

In a particular embodiment, the candidate compounds may be selected from small organic molecules. As used herein, the term "small organic molecule" refers to a molecule of size comparable to those organic molecules generally used in pharmaceuticals. The term excludes biological macromolecules (e.g., proteins, nucleic acids, etc.). Preferred small organic molecules range in size up to 2000 Da, and most preferably up to about 1000 Da.

In another particular embodiment, the candidate compound according to the invention may be an antibody. The antibodies of the invention can for instance be produced by any hybridoma liable to be formed according to classical methods from splenic cells of an animal, particularly of a mouse or rat immunized against an antigenic sequence of interest. The antibodies according to this embodiment of the invention may be humanized versions of the mouse antibodies made by means of recombinant DNA technology, departing from the mouse and/or human genomic DNA sequences coding for H and L chains or from cDNA clones coding for H and L chains. Alternatively, the antibodies may be human antibodies. Such human antibodies are prepared, for instance, by means of human peripheral blood lymphocytes (PBL) repopulation of severe combined immune deficiency (SCID) mice as described in PCT/EP99/03605 or by using transgenic non-human animals capable of producing human antibodies, as described in U.S. Pat. No. 5,545,806. Fragments derived from these antibodies, such as Fab, F(ab)'2 and s ("single chain variable fragment"), providing they have retained the original binding properties, also form part of the present invention. Such fragments are commonly generated by, for instance, enzymatic digestion of the antibodies with papain, pepsin, or other proteases. It is well known to the person skilled in the art that monoclonal antibodies or fragments thereof can be modified for various uses. An appropriate label of the enzymatic, fluorescent, or radioactive type can label the antibodies involved in the invention.

In some embodiments, the candidate compounds may be selected from aptamers. Aptamers are a class of molecule that represents an alternative to antibodies in terms of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consist of a conformationally constrained antibody variable region displayed by a platform protein, such as *E. coli* thioredoxin A, that are selected from combinatorial libraries by two hybrid methods (Colas et al., 1996).

In still another particular embodiment, the candidate compound may be selected from molecules that block expression of a gene of interest. Also within the scope of the invention is the use of oligoribonucleotide sequences that include anti-sense RNA and DNA molecules and ribozymes that function to inhibit the translation of mRNA of a nuclear protein required for Notch1 transcriptional activity. Antisense RNA and DNA molecules act to directly block the translation of mRNA by binding to targeted mRNA and preventing protein translation. In regard to antisense DNA, oligodeoxyribonucleotides are derived from the translation initiation site. Ribozymes are enzymatic RNA molecules capable of catalyzing the specific cleavage of RNA. The mechanism of ribozyme action involves sequence-specific hybridization of the ribozyme molecule to complementary target RNA, followed by an endonucleolytic cleavage. To inhibit the activity of the gene of interest or the gene product of the gene of interest, custom-made techniques are available directed at three distinct types of targets: DNA, RNA and protein. For example, the gene or gene product of a nuclear protein required for Notch1 transcriptional activity of the invention can be altered by homologous recombination, the expression of the genetic code can be inhibited at the RNA levels by antisense oligonucleotides, interfering RNA (RNAi) or ribozymes, and the protein function can be altered by antibodies or drugs.

The screening method of the invention is particularly suitable for identifying a compound that is a TLR antagonist, a TNF-alpha antagonist or an IL-1 antagonist.

In some cases, a candidate therapeutic agent has been identified and further testing may be required. In some embodiments the further testing is to evaluate a candidate therapeutic agent (or an agent that has been confirmed to be therapeutic) for quality control and/or safety concerns. In some embodiments, methods of the invention include a method of assaying a therapeutic agent (or candidate therapeutic agent) for efficacy against cancer, typically against a GIST or a renal cancer, in a relevant animal model.

The present invention also includes kits for assessing or monitoring the sensitivity of a subject having a tumor to a chemotherapy, wherein the kit comprises detection means, possibly in suitable containers, selected from the group consisting of at least one soluble B7-H6 polypeptide binding agent (typically an antibody specific to sB7H6), preferably in addition at least one soluble MIC polypeptide binding agent (typically an antibody specific to sMIC), and, optionally, a leaflet providing the sB7H6 reference expression level in a biological sample from a control or reference population. The kit may further comprise a means for determining the presence of a MICA-129 single nucleotide polymorphism (Boukouaci W et al., 2009, Blood, 114:5216), a low level of anti-MICA Ab and MICA-129 Val/Met being indicative of good prognosis for GIST patients.

In further embodiments, the binding agent is labeled or a detection agent is included in the kit. It is contemplated that the kit may include a B7-H6 and/or MIC polypeptide binding agent attached to a non-reacting solid support, such as a tissue culture dish or a plate with multiple wells. It is further contemplated that such a kit includes a detectable agent in certain embodiments of the invention. In some embodiments the invention concerns kits for carrying out a method of the invention comprising, in suitable containers: (a) an agent that specifically recognizes all or part of a B7-H6 or MIC polypeptide; and (b) a positive control that can be used to determine whether the agent is capable of specifically recognizing all or part of a B7-H6 or MIC polypeptide. The kit may also include other reagents that allow visualization or other detection of the B7-H6 or MIC polypeptide, such as reagents for colorimetric or enzymatic assays.

The invention will be further illustrated by the following figures and examples. However, these examples and figures should not be interpreted in any way as limiting the scope of the present invention.

(A) sB7H6 measured by ELISA in the sera at diagnosis of 75 renal cancer patients according to their segregation into the high/intermediate risk of relapse versus low risk of relapse (Motzer classification). The cut-off value has been set up according to the median value of the whole RCC cohort (4 ng/ml).

(B-C) Kaplan-Meier curves of EFS according to sB7H6 in the high and intermediate group (B) and low risk group (C) and segregated into sB7-H6>median or <median of the whole population. Log-Rank (Mantel-Cox): *p<0.05.

Figure 2:
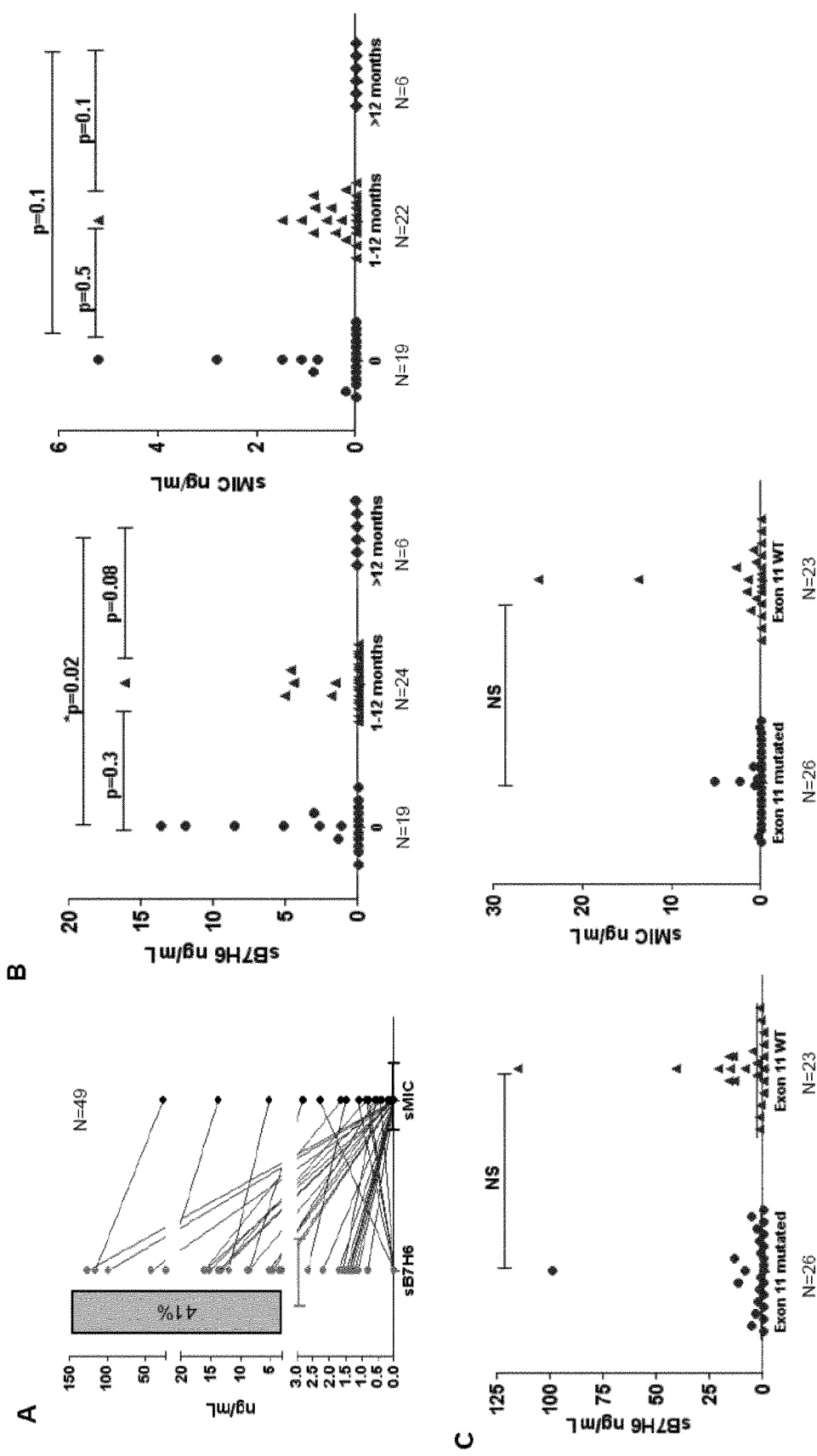

FIG. 2. Prognostic value of serum sB7H6 and sMIC in the natural course of primary GIST.

(A) Serum sB7H6 and sMIC values measured by ELISA (Vivier's laboratory) and correlated with each other for 49 GIST patients before IM treatment (paired analysis). The cut-off value is 3 ng/ml and values<3 ng/ml are considered negative. 41% GIST present with detectable sB7H6 at diagnosis.

(B) Serum sB7H6 and sMIC values measured by ELISA (Vivier's laboratory) longitudinally during IM treatment. sB7H6 (left panel) and sMIC (right panel) are shown.

(C) sB7H6 (left panel) and sMIC (right panel) are plotted according to the c-KIT exon 11 mutation (right: WT/non-mutated and left: mutated).

(D) The linear regression of NKp30 expression on NK (Mean Fluorescence Intensity (MFI) values, left panel) or NKp46 expression (MFI values, middle panel) and sB7H6 sera values. In comparison, linear regression of NKG2D expression (percentage values) and sMIC sera values (right panel) are shown.

(E) sB7H6 values are depicted according to the NKp30 isoform profile in PBMC for 26 GIST patients.

(F) B7H6 expression in freshly dissociated GIST tumors (MFI values) is shown according to NKp30 isoform profiling (performed in 10 GIST).

(G) Kaplan-Meier curves of EFS according to sera sB7H6 alone (left panel) and combined with sMIC values (right panel) at diagnosis (before treatment). The stratification on these values allows for 4 groups to be identified. Log-Rank (Mantel Cox): *p<0.05.

Figure 3:
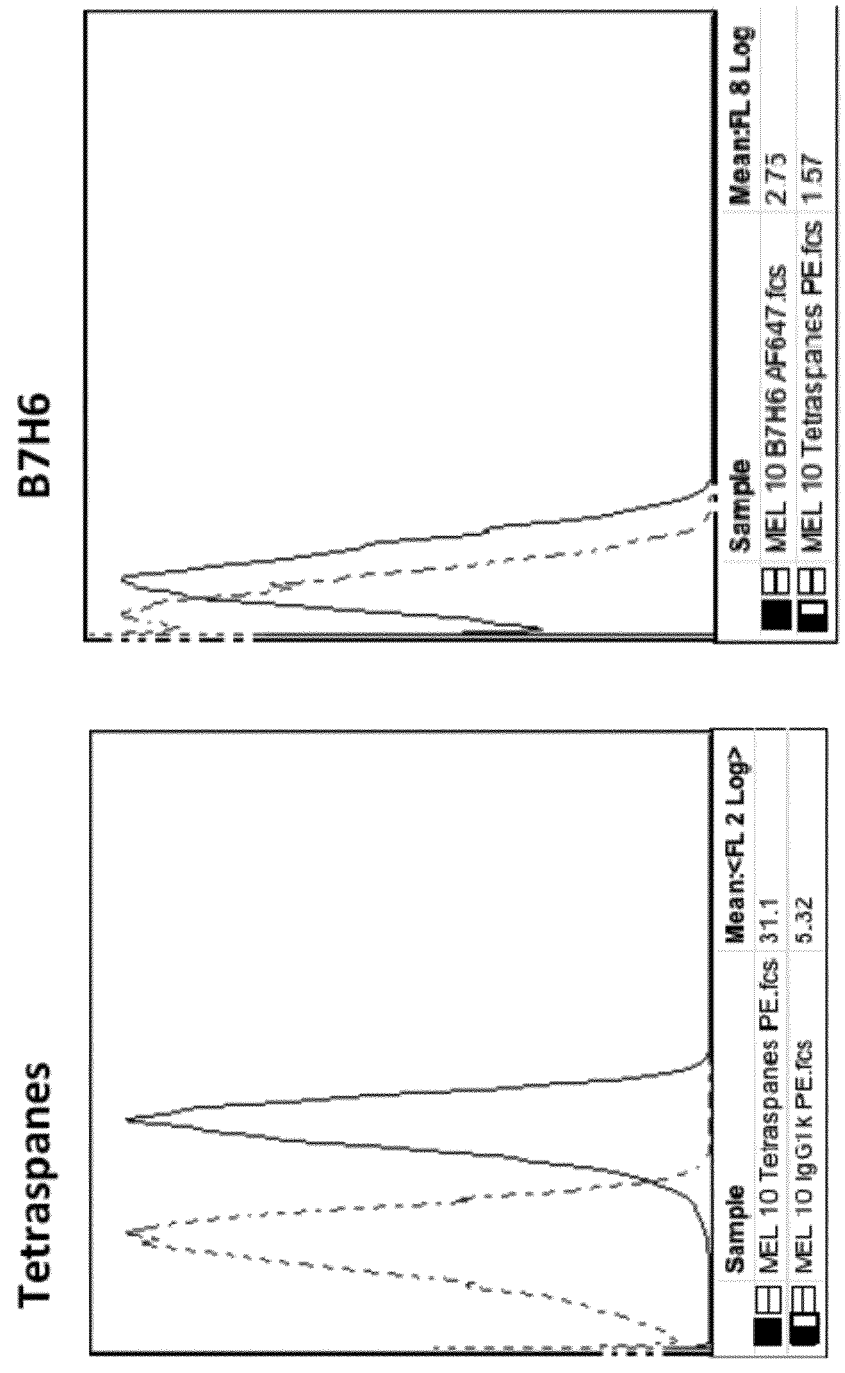

FIG. 3. sB7-H6 are harbored on tumor-derived exosomes and are functional molecules.

(A) Tumor-derived exosomes (TEX) from Mel10 melanoma (or control pellets) coated onto beads to analyze the MFI of B7-H6 or tetraspanins. TEX express low levels of B7-H6 on the external membranes of vesicles.

(B) TEX downregulates NKp30 expression levels on Jurkat CD4$^+$ cells genetically modified to express high levels of NKp30A isoform. Coculture of 1-10 ug of TEX (or control pellets) with 100,000 CD4+ Jurkat-NKp30A cells for 24 hours. Flow cytometry analysis showing an overlay of MFI (upper panels) and a graph (lower panels).

(C) Levels of human IFNg in the supernatants of the same experiments, as monitored at 24 hours of coculture.

Figure 4:
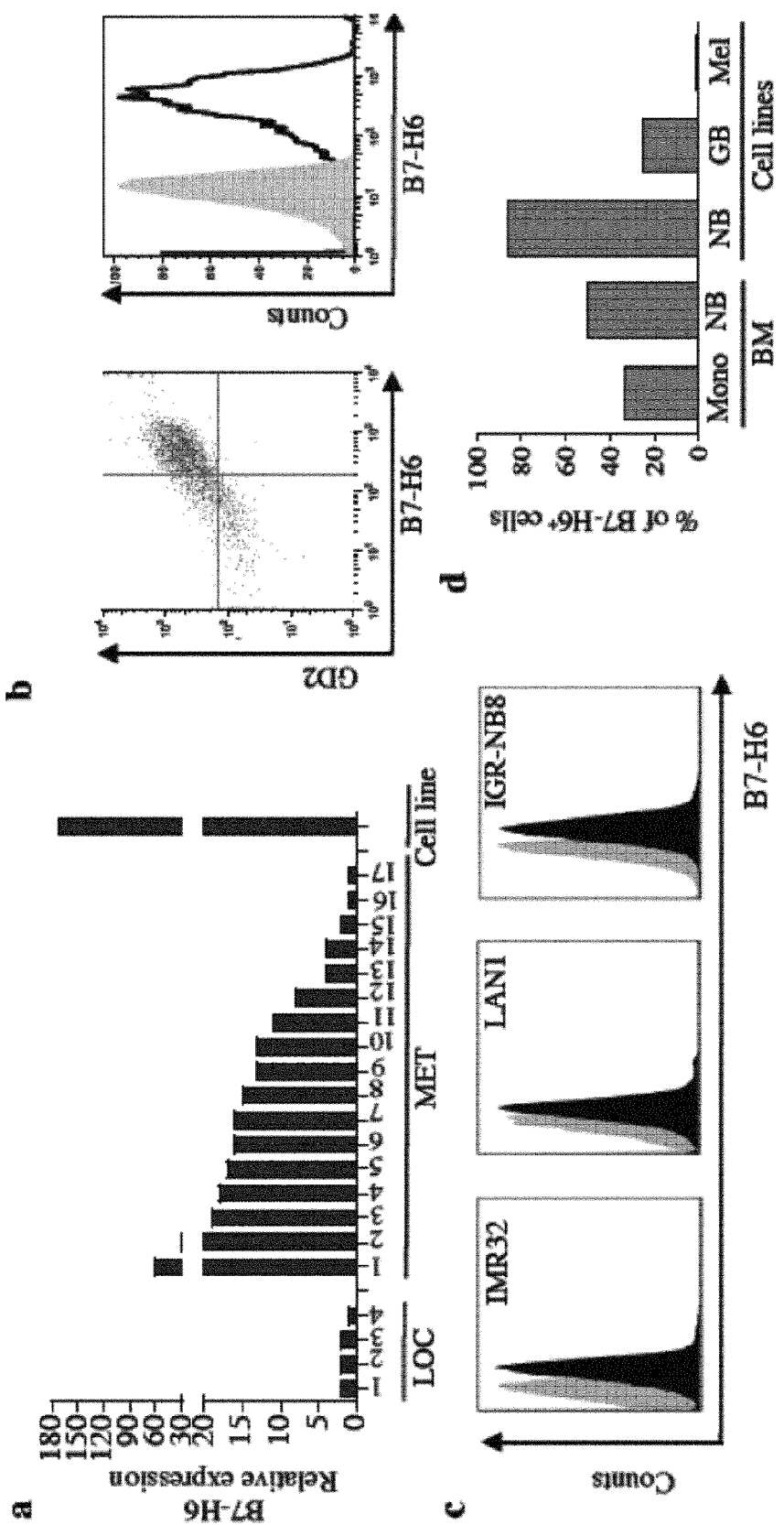

FIG. 4. B7-H6 expression by neuroblasts associated with accumulation of sB7-H6 in serum.

a-d. qRT-PCR and protein determination of B7-H6 expression on neuroblastoma. mRNA levels were analyzed in qRT-PCR using specific primers in 17 metastatic and 4 localized NB. IGR-NB-8 is a cell line exhibiting a positive membrane expression of B7-H6 (a). BM cells were analyzed in flow cytometry gating on CD45$^-$GD2$^+$NB cells (b, left panel) for the expression of B7-H6 molecules (thick lines). A dot plot as well as an overlay of a representative flow cytometry analysis is depicted (b, right panel). The isotype control is a grey plotted line (b). Constitutive expression of B7-H6 as determined by flow cytometry on three NB cell lines. The isotype control antibody is shown with a grey plotted line (c). The proportions of B7-H6 expressing cells, i.e., BM monocytes (positive expression N=2/6) and GD2- positive neuroblasts (positive expression N=2/4) and on neuroectodermal cell lines (NB=neuroblastoma (N=8), GB=glioblastoma (N=4), Mel=melanoma (N=5)) are indicated (d). e-g. Soluble B7-H6 in sera of HR-NB. ELISA (detailed in M&M) were performed in the sera of 20 metastatic NB and 5 localized NB at diagnosis and analyzed according to NKp30 expression on peripheral NK$^{dim}$ cells in metastatic patients (cut-off value=60% established on HD, FIG. 2a, left panel) (e), as well as to the dissemination of the disease as assessed by bone scan (MIBG-SIOPEN criteria) (f) and to the response to induction chemotherapy in metastatic patients (g). Threshold of sB7-H6 detection has been set at 0.6 ng/ml. Normal individuals present sB7-H6 with concentrations below 3 ng/ml (not shown). * $p<0.05$, ** $p<0.01$. ns, not significant in Mann-Whitney analyses. CR: complete response; PR: partial response; MR: minimal response; NR: no response

REFERENCES

Throughout this application, various references describe the state of the art to which this invention pertains. The disclosures of these references are hereby incorporated by reference into the present disclosure.

Figure 1:
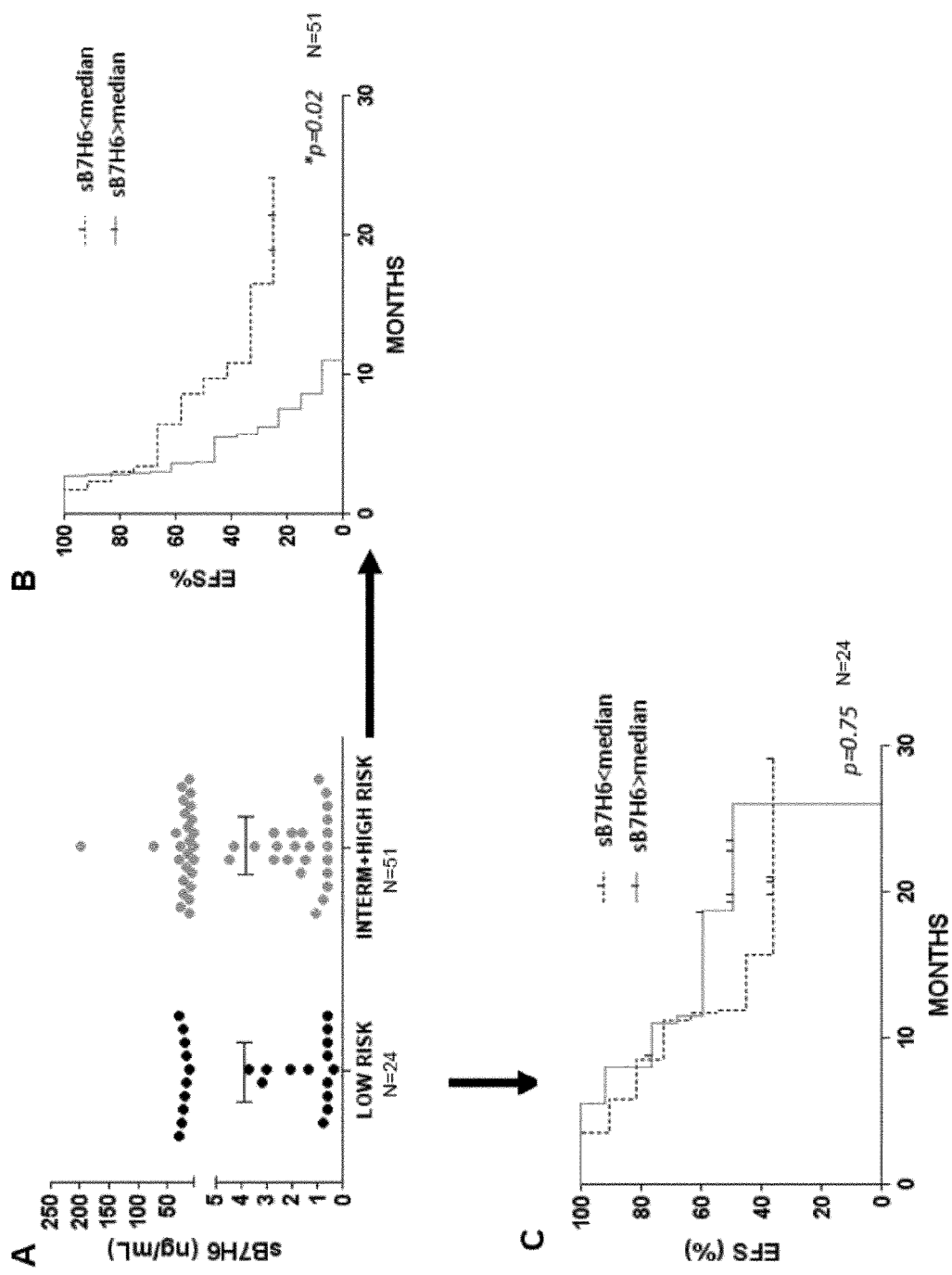
FIG. 1. sB7H6 levels are negative prognosis markers in high/intermediate risk metastatic renal cancer.

Other characteristics and advantages of the invention are given in the following experimental section (with reference to FIGS. 1 to 3), which should be regarded as illustrative and not limiting the scope of the present application.

EXPERIMENTAL PART

Example 1

Prognostic Value of sB7H6 and sMIC in the Natural Course of Primary GIST and Metastatic Renal Cancer Materials and Methods Patient Specimens.

This experience was carried out on 75 metastatic renal cancer patients from a TORAVA cohort (Negrier S et al., 2011, Lancet Oncol. 12:673) treated with a combination of bevacizumab and temsirolimus, or one of the two following standard treatments, i.e., either sunitinib or the combination of interferon alpha and bevacizumab. 49 GIST patients were treated with imatinib (IM) from May 1994 until October 2010 (BFR14 cohort). Patients' samples were provided by the Gustave Roussy Institute (Villejuif, France) and the Centre Léon Bérard (Lyon). Sera were drained from blood drawn during control visits. Clinical responses were assessed by computed tomography (CT) scan and the responses were classified according to the RECIST criteria. GIST tumor samples were obtained following surgery carried out at the Gustave Roussy Institute (Villejuif, France).

sB7H6 and sMIC Detection.

sB7H6 and sMIC were assessed from the sera of patients by the ELISA method.

Exosome Production and Purification from Mel 10 Cell Line.

Mel 10 TEX (texosomes) were produced and purified following the procedure described elsewhere (Viaud S et al., 2009, PLOS ONE, 4:e4942; Lamparski H G, et al., 2002, J Immunol methods, 270:211).

Functional Assay.

1 or 10 µg/mL of Mel 10 TEX or control pellets were incubated with 0.5×10$^6$ WT Jurkat cells or Jurkat cells modified to express the NKp30 A isoform receptor for 24 hours at 37° C. Then WT or NKp30A-expressing Jurkat cells were harvested and stained with NKp30 Ab (Miltenyi) and viability marker. Cells were then acquired on a CyAn flow cytometer (Beckman Coulter) and analyzed using FlowJo software (Tree Star). IFNg was measured from the supernatant using a commercial ELISA kit (BD OptEIA, Cliniscience). In some experiments, GIST fresh tumors were obtained and dissociated following the gentle MACS Dissociator protocol (Miltenyi). Then the dissociated tumor cells were stained with B7H6 Ab and viability marker.

Statistical Analyses.

The linear regression test and the non-parametric Mann-Whitney test were used for comparison of the different groups. These statistical analyses were performed with the GraphPad Prism software, version 5. The survival curves were plotted according to the Kaplan-Meier method, and compared using the log-rank test (Mantel-Cox).

Results sB7H6 Levels are Negative Prognosis Markers in High/Intermediate Risk Metastatic Renal Cancer First, the inventors measure the sB7H6 level in sera of 75 renal cancer patients at diagnosis. There is no difference in the level of sB7H6 detected in patients according to their segregation into high/intermediate risk of relapse versus low risk of relapse (Motzer classification, Motzer R J et al., 1999, J Clin Oncol, 17:2530) (FIG. 1A). However, in the high/intermediate risk kidney cancer group, the Kaplan-Meier curves of event free survival (EFS) shows that patients with a sB7H6 level higher than the median (4 ng/ml) have a shorter EFS % than the patients with a sB7H6 level lower than the median (4 ng/ml) (FIG. 1B). In the low risk of relapse kidney cancer group, the Kaplan-Meier curves of EFS show no difference between the two groups of patients (FIG. 1C).

These results indicate that sB7H6 levels in the sera of high/intermediate risk of relapse renal cancer patients detected at diagnosis are negative prognostic markers of response to treatment with IFNa +/− bevacizumab, mTOR inhibitor+/−bevacizumab, and sunitinib.

Prognostic Value of Serum sB7H6 and sMIC in the Natural Course of Primary GIST

The inventors measure the sB7H6 and sMIC levels in sera of 49 GIST patients at diagnosis. 41% of GIST patients present sB7H6 above the cut-off value of 3 ng/mL at diagnosis (FIG. 2A).

Then the levels of sB7H6 and sMIC are followed during IM treatment. The levels of sB7H6 decreased with the time of treatment and are not detected after 1 year of IM treatment (FIG. 2B, left panel). The levels of sMIC also tend to decrease following IM treatment (FIG. 2B, right panel).

There is no correlation between the levels of sB7H6 or sMIC detected in the sera of GIST patients and their c-KIT exon 11 mutation (FIG. 2C, left and right panel respectively).

B7H6 is a natural ligand for the NKp30 receptor (Brandt C S et al., 2009, J Exp Med, 206:1495) and NKp30 receptors are involved in GIST cancer (Delahaye N F et al., 2011, Nat Med, 17:700); thus, the inventors investigated the correlation between sB7H6 and expression of NKp30 (or of the irrelevant NKp46) on the one hand and the correlation between sMIC and the expression of NKG2D (sMIC is a ligand of NKG2D) on the other hand. The inventors showed that there is a trend of linear regression between sB7H6 and NKp30 (FIG. 2D, left panel) but not with NKp46 (FIG. 2D, middle panel). There was no correlation between sMIC sera levels and NKG2D expression in these patients (FIG. 2D, right panel). These data indicate that sB7-H6 promotes the downregulation of circulating NKp30 (expressed on blood NK cells), which is usually associated with bad prognosis.

Then the inventors investigated the sB7H6 levels in sera according to the NKp30 isoform profile in PBMC. No correlation between sB7H6 level and NKp30 isoform profile was found (FIG. 2E). However, 2/3 of GIST patients with an NKp30 isoform profile AB have no membrane B7H6 detected on their freshly dissociated GIST tumor cells (FIG. 2F), suggesting that an immunoediting process against B7-H6 might occur in tumor beds.

The inventors investigated the event-free survival (EFS) of the GIST patients according to their sB7H6 levels. The Kaplan-Meier curves of EFS show that patients with positive sB7H6 sera level (above the 3 ng/ml cut-off value) tend to have a shorter EFS % than the patients with negative sB7H6 (FIG. 2G, left panel).

Then the inventors investigated the EFS of the GIST patients according to their sB6H7 levels combined with sMIC levels. The Kaplan-Meier curves of EFS show that patients with a positive sB7H6 level and negative sMIC level (20% of patients) have a shorter EFS % than the patients with a negative sB7H6 level but positive sMIC level (FIG. 2G, right panel).

These results indicate that sB7H6 levels combined with sMIC level measured in the sera of GIST patients at diagnosis are prognostic markers of response to imatinib treatment.

sB7-H6 are Harbored on Tumor-Derived Exosomes (TEX or Texosomes) and are Functional Molecules Tumor-derived exosomes (TEX) from a melanoma cell line (Mel10) positive for B7H6 were produced to assess the bioactivity of sB7H6. The inventors first tested the expression of tetraspanins (exosome-specific) and sB7H6 on the external membranes of Mel10-derived TEX vesicles (FIG. 3A). Then the inventors investigated the capacity of Mel10 TEX (or negative control pellets of Mel10 exosomes) to bind and subsequently signal via NKp30 isoform A-transduced Jurkat T cell lines. Mel10 TEX, but not control pellets, downregulates NKp30 expression on Jurkat T cell lines modified to express high levels of NKp30 A isoform, in a dose-dependent manner (FIG. 3B, upper and lower panels). Following Mel10 TEX engagement with NKp30 expressing Jurkat cells, but not WT Jurkat cells, IFNg was detected in the supernatant of cocultures. Thus, sB7H6 expressed on tumor-derived exosomes binds to their receptors and are functional molecules.

Example 2

Prognostic Value of sB7H6 in High Risk Neuroblastoma (HR-NB) and Predictive Value of sB7H6 as a Biomarker of Chemoresistance in HR-NB High Risk Neuroblastoma (HR-NB) is a poor-prognosis pediatric malignancy with 5-year survival rates of up to 30% despite intensive multimodal treatment. Age, stage, MYCN amplification, chromosomal abnormalities and, more recently, tumor infiltration with inflammatory cells are prognostic markers. NB is amenable to immunotherapy based on the activation of monocytes and/or natural killer (NK) cells. HR-NB can be distinguished from localized NB by abnormal proportions of NK cells in blood and bone marrow exhibiting a selective downregulation of NKp30 expression, which is associated with resistance to induction chemotherapy.

Materials and Methods

Patients and Specimens:

The immunomonitoring study was carried out on a total of 48 fresh peripheral blood samples (12 from localized NBs and 36 from metastatic NBs) and 12 fresh bone marrow blood samples from metastatic NB patients all at the time of diagnosis. The Pediatric Department of Gustave Roussy Institute (Villejuif, France) provided all patients' samples, and informed written consent was obtained according to the guidelines of the local ethical committee. Healthy volunteers' PBMC samples were obtained from the Gustave Roussy Institut bio-bank (CRB: Centre Ressources Biologiques).

Immunomonitoring-Phenotyping:

Nine-color flow cytometry analysis was performed on freshly harvested blood cells. Cells were incubated with conjugated antibodies for 20 minutes in the dark, washed and fixed with 1% paraformaldehyde. Stained cells were acquired within 24 hours on a CyAn flow cytometer (Beckman Coulter) and analyzed using FlowJo software (Tree Star).

Cell Lines and Culture:

The human NB cell lines SH-SY5Y, NJB, IGR-N91, IGR-NB8, LAN-1, SK-N-SH, SK-N-BE, and IMR-32 were kindly provided by Prof. G. Vassal, Pharmacology and New Treatments of Cancer-UPRES-EA-Institut Gustave Roussy. Cell lines were maintained in Dulbecco's modified Eagle medium (DMEM) (Invitrogen, Life Technologies) supplemented with 10% heat-inactivated fetal bovine serum (Invitrogen, Life Technologies) or in R10 medium, consisting of RPMI medium (Invitrogen, Life Technologies) with 10% heat-inactivated fetal bovine serum (Invitrogen, Life Technologies), 1% sodium pyruvate, 5 mM L-glutamine, and 1% Peni-Strepto in 5% $CO_2$ at 37° C.

Monitoring of B7-H6 and Soluble B7-H6:

Fresh bone marrow blood samples from 4 infiltrated bone marrow NBs at diagnosis were stained with conjugated antibodies, detailed in Table 1 below, to determine B7-H6 expression (Anti-B7-H6 mAbs (17B1.3) APC conjugated) on neuroblasts (CD45-, CD235ab CD9/CD81+, CD56+ and GD2+) and monocytes (CD45+, CD14+).

TABLE 1

Details of antibodies (Ab) utilized for the immunophenotyping

| Ab | Clone | Conjugated | Company |
|---|---|---|---|
| CD8 | RPA-T8 | PerCP | BD |
| NKp46 | 9E2 | APC | Miltenyi |
| CD4 | SK3BD | PECy7 | BD |
| CD16 | 3G8 | Pacific Blue | BD |
| CD56 | N901 | PECy7 | Beckman Coulter |
| NKp30 | AF29-4D12 | PE | Miltenyi |
| NKG2D | BAT221 | APC | Miltenyi |
| DNAM-1 | 102511 | FITC | R&D |
| CD127 | hIL-7R-M21 | FITC | BD |
| CD25 | 2A3 | PE | BD |
| CD14 | TUK4 | PerCP | Miltenyi |
| CD45 | J33 | APC-Alexa Fluor 750 | Beckman Coulter |
| CD15 | HI98 | PE | BD |
| GD2 | 14.G2a | unconjugated | BD |
| CD235a | HIR2 | PerCP | BD |
| CD9 | MZ3 | PE | Biolegend |
| CD81 | JS64 | PE | Beckman Coulter |
| TCRγδ | B1 | FITC | BD |
| NKp44 | 2.29 | APC | Miltenyi |
| NKp80 | 239127 | FITC | R&D |
| CD3 | SP34-2 | Pacific Blue | Miltenyi |
| CD158 a, h | 11PB6 | FITC | Miltenyi |
| CD158b | DX27 | PerCP | Miltenyi |

TABLE 1-continued

Details of antibodies (Ab) utilized for the immunophenotyping

| Ab | Clone | Conjugated | Company |
|---|---|---|---|
| CD158e, k | 5.133 | PE | Miltenyi |
| CD158i | JJC11.6 | APC | Miltenyi |

Staining with Anti-B7-H6 mAbs (17B1.3) was also performed on NB cell lines. Phenotyping was performed as described before. Stainings were analyzed on a CyAn flow cytometer (Beckman Coulter) using FlowJo software (Tree Star, Inc.).

Soluble B7-H6 detection was assessed from sera of patients by the ELISA method: 17B1.3 mAbs was coated at 5 µg/ml in 0.1 M NaHCO$_3$ solution overnight at 4° C. in 96-well Nunc-Immuno™ plates (Thermo Scientific). Blocking solution (PBS supplemented with 3% BSA) was then added overnight at 4° C. After discarding this solution, serial dilutions of sB7-H6 were incubated for 3 hours at room temperature. Then biotin-conjugated 9G9.2 was added to each well (1 µg/ml in PBS supplemented with 1% BSA) for 1 hour at room temperature. Anti-biotin HRP (Sigma-Aldrich) was then added for 1 hour at room temperature. Finally, BD Optia TMB substrate (BD Biosciences) was used to reveal the staining and left to incubate for 15-30 minutes at room temperature. The reaction was stopped with 1 M HCl and the optic density (OD) at 450 nm was read with Apollo LB 911 from Berthold.

Results

While B7-H6 transcripts have not been detected in most normal adult tissues, they were highly detectable in most of the 17 BM specimens from metastatic NBs that were analyzed while none were detectable in 4/4 localized NBs (FIG. 4a). While originally described in leukemia and some primary cancer lines, B7-H6 surface expression could be observed in 2 out of 4 cases in the GD2$^+$ neuroblast cell fraction of the bone marrow (BM) (FIG. 4b). Moreover, all the NB cell lines tested expressed constitutive levels of B7-H6 (FIGS. 4c-d and not shown). The inventors monitored serum levels of sB7-H6 in HR-NB patients. High concentrations of sB7-H6 were found in the serum of metastatic patients and were associated with an abnormally low NKp30 expression on CD3$^-$CD56$^{dim}$ NK cells (FIG. 4e). Importantly, sB7-H6 serum levels were associated with NB dissemination (FIG. 4f) and tumor progression despite therapy (FIG. 4g).

Altogether, these data indicate that B7-H6 is overexpressed in invaded BM of HR-NB and its soluble form is associated with NKp30 downregulation as well as metastatic spreading and resistance to chemotherapy. Interestingly, these data corroborate those obtained in another tumor type of mesenchymal origin, namely gastrointestinal stromal tumor (GIST), as apparent from example 1.

The invention claimed is:

1. A method of treating a gastrointestinal sarcoma (GIST) in a subject, the method comprising the steps of:
   a) determining, in a biological sample of said subject, the expression level of soluble B7H6 (sB7H6) and the presence or absence of soluble MIC (sMIC) in an enzyme linked immunosorbent assay (ELISA);
   b) comparing said expression level of sB7H6 in the biological sample of the subject to a sB7H6 reference expression level in an ELISA; and
   c) treating GIST in the subject by administering to the subject:
      i) imatinib in combination with an appropriate chemotherapeutic treatment when:
         a) the expression level of sB7H6 in the biological sample of the subject is above the sB7H6 reference expression level of about 3 ng/ml, or
         b) the expression level of sB7H6 in the biological sample of the subject is above the sB7H6 reference expression level of about 3 ng/ml and sMIC is absent in the biological sample of the subject: or
      ii) imatinib alone when:
         a) the expression level of sB7H6 in the biological sample of the subject is below the sB7H6 reference expression level of about 3 ng/ml, or
         b) the expression level of sB7H6 in the biological sample of the subject is below the sB7H6 reference expression level of about 3 ng/ml and sMIC is present in the biological sample of the subject;
   wherein the appropriate chemotherapeutic treatment comprises an anti-B7-H6 neutralizing antibody and an immunomodulator stimulating T and/or NK cell production or activity, and
   wherein the sB7H6 reference expression level is the level of the sB7H6 polypeptide in one or more control samples derived from one or more individuals having GIST.

2. The method according to claim 1, wherein the immunomodulator stimulating and/or NK cell production or activity is anti-PD-1 antibody, anti-PDL-1 antibody, anti-CTLA4 monoclonal antibody, a double strand RNA (Poly I:C, Poly A:U), a type 1 IFN (alpha2b), IL-2, an inhibitor of IL-1/IL-1R1, an inhibitor of TNFa/TNFR, a TLR7 antagonist, a TLR8 antagonist, a TLR9 antagonist or any combination thereof.

3. The method according to claim 1, wherein the biological sample is serum.

4. An in vitro method for determining whether the expression of sB7H6 in a serum sample of a subject is above or below a sB7H6 reference expression level, the method comprising the steps of:
   (a) contacting the serum sample from the subject with an antibody specific to sB7H6 for a time and under conditions allowing the formation of complexes between sB7H6 present in the serum sample and the antibody specific to sB7H6;
   (b) detecting the formation of said complexes using a system generating quantifiable signal;
   (c) determining whether the expression of sB7H6 in the biological sample of the subject is above or below the sB7H6 reference expression level,
   wherein the sB7H6 reference expression level is between 0 and 4 ng/ml.

5. The method according to claim 4, wherein the sB7H6 reference expression level is 3 ng/ml.

* * * * *

UNITED STATES PATENT AND TRADEMARK OFFICE
CERTIFICATE OF CORRECTION

PATENT NO. : 9,557,333 B2  
APPLICATION NO. : 14/429789  
DATED : January 31, 2017  
INVENTOR(S) : Eric Vivier and Laurence Zitvogel Page 1 of 1

It is certified that error appears in the above-identified patent and that said Letters Patent is hereby corrected as shown below:

In the Specification

Column 2,
Line 33, "receptor a" should read --receptor α--.

Column 14,
Line 59, "CD45⁻GD2⁺NB" should read --CD45⁻GD2⁺ NB--.

Column 18,
Line 40, "CD235ab CD9/CD81+," should read --CD235ab-, CD9/CD81+,--.
Line 45, "Details of antibodies (Ab) utilized for the immunophenotyping" should read --Details of antibodies (Ab) utilized for immunophenotyping--.

Column 19,
Line 2, "Details of antibodies (Ab) utilized for the immunophenotyping" should read --Details of antibodies (Ab) utilized for immunophenotyping--.

Signed and Sealed this
First Day of August, 2017

Joseph Matal
*Performing the Functions and Duties of the
Under Secretary of Commerce for Intellectual Property and
Director of the United States Patent and Trademark Office*